US009125819B2

(12) United States Patent
Yamamoto

(10) Patent No.: US 9,125,819 B2
(45) Date of Patent: Sep. 8, 2015

(54) ACTIVATED FOAM

(75) Inventor: Tomizo Yamamoto, Osaka (JP)

(73) Assignees: Tomizo Yamamoto, Osaka (JP); Hiroki Shima, Osaka (JP)

( * ) Notice: Subject to any disclaimer, the term of this patent is extended or adjusted under 35 U.S.C. 154(b) by 0 days.

(21) Appl. No.: 12/855,089

(22) Filed: Aug. 12, 2010

(65) Prior Publication Data

US 2010/0316718 A1    Dec. 16, 2010

Related U.S. Application Data

(62) Division of application No. 10/582,801, filed as application No. PCT/JP2005/008906 on May 16, 2005, now abandoned.

(30) Foreign Application Priority Data

Apr. 29, 2005   (JP) .................................. 2005-160403

(51) Int. Cl.
| | |
|---|---|
| A61K 9/14 | (2006.01) |
| A61K 9/12 | (2006.01) |
| A61K 9/70 | (2006.01) |
| A61K 33/24 | (2006.01) |
| A61K 33/44 | (2006.01) |
| A61K 45/06 | (2006.01) |

(52) U.S. Cl.
CPC ................ *A61K 9/122* (2013.01); *A61K 9/7023* (2013.01); *A61K 33/24* (2013.01); *A61K 33/44* (2013.01); *A61K 45/06* (2013.01)

(58) Field of Classification Search
USPC ......................................................... 424/485
See application file for complete search history.

(56) References Cited

U.S. PATENT DOCUMENTS

| | | | |
|---|---|---|---|
| 3,644,235 A | 2/1972 | Gray | |
| 4,890,872 A | 1/1990 | Parrotta et al. | |
| 6,007,817 A * | 12/1999 | Epstein et al. | ............. 424/178.1 |
| 6,455,610 B1 | 9/2002 | Lever et al. | |
| 7,056,883 B2 | 6/2006 | Ito et al. | |
| 2002/0017734 A1* | 2/2002 | Sugihara et al. | ................ 264/51 |
| 2004/0018184 A1 | 1/2004 | Bartholeyns et al. | |
| 2004/0018968 A1* | 1/2004 | Sgouros et al. | ................... 514/9 |

FOREIGN PATENT DOCUMENTS

| | | |
|---|---|---|
| JP | 56-141333 | 11/1981 |
| JP | 01-182030 | 7/1989 |
| JP | 03-047126 | 2/1991 |
| JP | 4-089051 | 3/1992 |
| JP | 04-187634 | 7/1992 |
| JP | 06-005949 | 1/1994 |
| JP | 06-321789 | 11/1994 |
| JP | 7-096045 | 4/1995 |
| JP | 3041702 | 7/1997 |
| JP | 10-120581 | 5/1998 |
| JP | 10-245703 | 9/1998 |
| JP | 11-116488 | 4/1999 |
| JP | 11-302173 | 11/1999 |
| JP | 11-310537 | 11/1999 |
| JP | 2000-034228 | 2/2000 |
| JP | 2002-510639 | 4/2002 |
| JP | 2002-510656 | 4/2002 |
| JP | 2002-219182 | 8/2002 |
| JP | 2003-002826 | 1/2003 |
| JP | 2003-082141 | 3/2003 |
| JP | 2003-516441 | 5/2003 |
| JP | 2003-160774 | 6/2003 |
| JP | 2003-268143 | 6/2003 |
| JP | 2003-231638 | 8/2003 |
| JP | 2003-238398 | 8/2003 |
| JP | 2005-002374 | 1/2005 |
| JP | 3107831 | 2/2005 |
| RU | 2 147 222 | 4/2000 |
| WO | 02/062403 | 8/2002 |

OTHER PUBLICATIONS

Machine translation of Jp 2003-160774.*
Sesto (PNAS, Mar. 5, 2002, vol. 99, No. 5, 2965-2970).*
Wang (J. Biol. Chem. 2003, 278:23861-23867).*
Gillenwater (Head & Neck vol. 22, Issue 3, pp. 247-256, May 2000).*
Cousens, "Different Accessibilities in Chromatin to Histone Acetylase," Journal of Biological Chemistry, vol. 254, No. 5, pp. 1716-1723 (1979).
Japanese Office Action issued Nov. 25, 2013 in corresponding Japanese Application No. 2006-536494.

* cited by examiner

*Primary Examiner* — David J Blanchard
*Assistant Examiner* — Devang Thakor
(74) *Attorney, Agent, or Firm* — Wenderoth, Lind & Ponack, L.L.P.

(57) ABSTRACT

The present invention relates to an activated foam made of a natural or synthetic rubber or a synthetic resin, characterized in that the foam contains a zirconium compound and/or a germanium compound, and has a closed-cell structure, wherein the foam is used so as to directly or indirectly contact with a human body when a pharmaceutical agent is administered. The activated foam can be directly or indirectly contacted with a human body to facilitate blood circulation and promote the improvement of physical condition and the cure of diseases. It also has no adverse effect.

6 Claims, 10 Drawing Sheets

Fig. 8
Du145 (+)
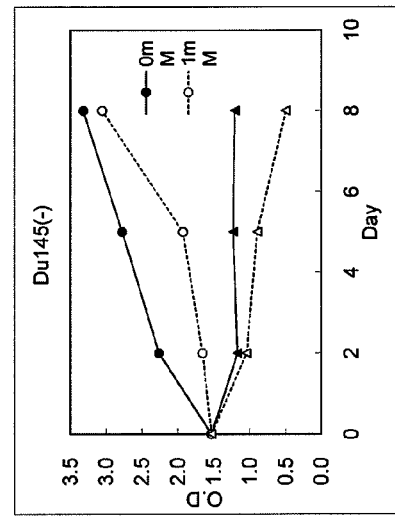
Du145 (−)
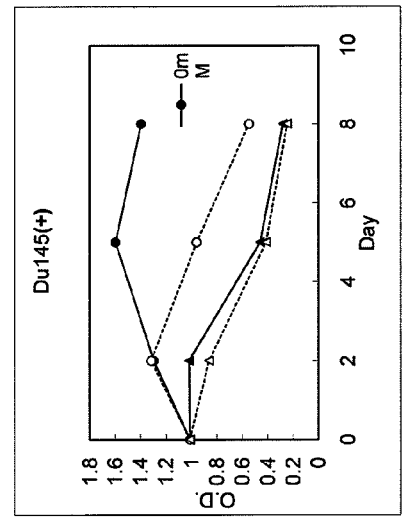

Fig. 9
LNCap (+)
| | | 0Day | 2Day | 5Day | 8Day |
|---|---|---|---|---|---|
| 0mM | | 0.745 | 0.392 | 1.197 | 0.648 |
| | | 0.841 | 0.412 | 1.662 | 0.690 |
| | | 0.775 | 0.417 | 1.524 | 0.657 |
| | | 0.763 | 0.421 | 1.328 | 0.687 |
| | Average | 0.781 | 0.411 | 1.428 | 0.671 |
| | STDEV | 0.042 | 0.013 | 0.206 | 0.021 |
| 1mM | | 0.745 | 0.394 | 0.980 | 0.429 |
| | | 0.841 | 0.354 | 1.097 | 0.433 |
| | | 0.775 | 0.381 | 0.970 | 0.440 |
| | | 0.763 | 0.397 | 0.862 | 0.440 |
| | Average | 0.781 | 0.382 | 0.977 | 0.436 |
| | STDEV | 0.042 | 0.020 | 0.096 | 0.005 |
| 2mM | | 0.745 | 0.360 | 0.858 | 0.380 |
| | | 0.841 | 0.330 | 0.739 | 0.383 |
| | | 0.775 | 0.352 | 0.809 | 0.382 |
| | | 0.763 | 0.335 | 0.663 | 0.361 |
| | Average | 0.781 | 0.344 | 0.767 | 0.377 |
| | STDEV | 0.042 | 0.014 | 0.085 | 0.010 |
| 3mM | | 0.745 | 0.340 | 0.691 | 0.344 |
| | | 0.841 | 0.358 | 0.643 | 0.344 |
| | | 0.775 | 0.351 | 0.644 | 0.321 |
| | | 0.763 | | 0.698 | |
| | Average | 0.781 | 0.350 | 0.669 | 0.336 |
| | STDEV | 0.042 | 0.009 | 0.030 | 0.013 |
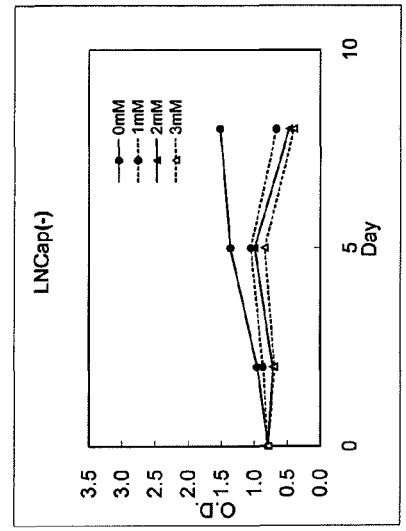
LNCap (−)
| | | 0Day | 2Day | 5Day | 8Day |
|---|---|---|---|---|---|
| 0mM | | 0.778 | 0.855 | 1.419 | 1.691 |
| | | 0.836 | 1.059 | 1.357 | 1.592 |
| | | 0.830 | 1.012 | 1.379 | 1.567 |
| | | 0.731 | 0.914 | 1.318 | 1.236 |
| | Average | 0.794 | 0.960 | 1.368 | 1.522 |
| | STDEV | 0.049 | 0.092 | 0.042 | 0.198 |
| 1mM | | 0.778 | 0.840 | 1.060 | 0.726 |
| | | 0.836 | 0.906 | 1.076 | 0.669 |
| | | 0.830 | 0.871 | 1.019 | 0.635 |
| | | 0.731 | 0.867 | 1.067 | 0.659 |
| | Average | 0.794 | 0.871 | 1.056 | 0.672 |
| | STDEV | 0.049 | 0.027 | 0.025 | 0.039 |
| 2mM | | 0.778 | 0.728 | 0.977 | 0.427 |
| | | 0.836 | 0.763 | 0.985 | 0.465 |
| | | 0.830 | 0.726 | 1.061 | 0.507 |
| | | 0.731 | 0.680 | 0.972 | 0.534 |
| | Average | 0.794 | 0.724 | 0.999 | 0.483 |
| | STDEV | 0.049 | 0.034 | 0.042 | 0.047 |
| 3mM | | 0.778 | 0.728 | 0.876 | 0.396 |
| | | 0.836 | 0.658 | 0.814 | 0.429 |
| | | 0.830 | 0.708 | 0.880 | 0.401 |
| | | 0.731 | 0.698 | 0.828 | 0.402 |
| | Average | 0.794 | 0.698 | 0.850 | 0.407 |
| | STDEV | 0.049 | 0.029 | 0.033 | 0.015 |
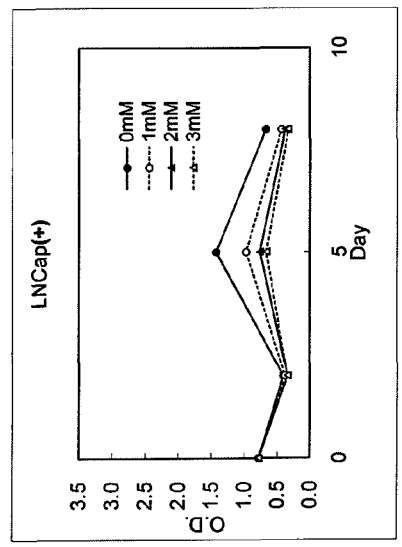

Fig. 10
PC3 (+)
| | | 0Day | 2Day | 5Day | 8Day |
|---|---|---|---|---|---|
| 0mM | | 0.407 | 0.275 | 2.777 | 1.289 |
| | | 0.497 | 0.256 | 2.662 | 1.023 |
| | | 0.450 | 0.273 | 0.277 | 1.056 |
| | | 0.428 | 0.253 | 3.034 | 0.905 |
| | Average | 0.446 | 0.264 | 2.188 | 1.068 |
| | STDEV | 0.039 | 0.011 | 1.283 | 0.161 |
| 1mM | | 0.407 | 0.196 | 0.232 | 0.583 |
| | | 0.497 | 0.247 | 2.481 | 0.659 |
| | | 0.450 | 0.242 | 2.457 | 0.677 |
| | | 0.428 | 0.282 | 2.613 | 0.828 |
| | Average | 0.446 | 0.242 | 1.946 | 0.687 |
| | STDEV | 0.039 | 0.035 | 1.145 | 0.103 |
| 2mM | | 0.407 | 0.232 | 1.795 | 0.258 |
| | | 0.497 | 0.245 | 1.891 | 0.325 |
| | | 0.450 | 0.223 | 2.110 | 0.317 |
| | | 0.428 | 0.192 | 1.624 | 0.312 |
| | Average | 0.446 | 0.223 | 1.855 | 0.303 |
| | STDEV | 0.039 | 0.023 | 0.203 | 0.030 |
| 3mM | | 0.407 | 0.197 | 1.171 | 0.176 |
| | | 0.497 | 0.201 | 1.164 | 0.153 |
| | | 0.450 | 0.195 | 1.363 | 0.200 |
| | | 0.428 | 0.174 | 1.233 | 0.196 |
| | Average | 0.446 | 0.192 | 1.233 | 0.181 |
| | STDEV | 0.039 | 0.012 | 0.092 | 0.022 |
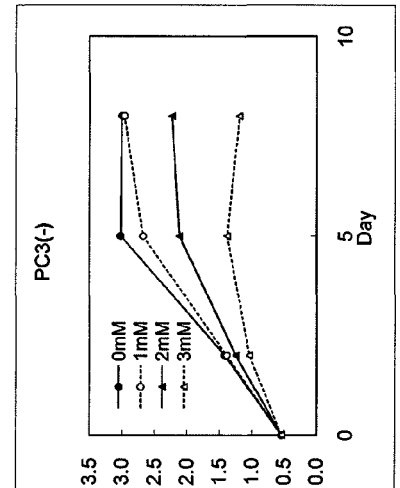
PC3 (−)
| | | 0Day | 2Day | 5Day | 8Day |
|---|---|---|---|---|---|
| 0mM | | 0.567 | 1.267 | 2.816 | 2.900 |
| | | 0.485 | 1.579 | 3.094 | 3.010 |
| | | 0.543 | 1.480 | 3.122 | 2.889 |
| | | 0.565 | 1.323 | 3.040 | 3.211 |
| | Average | 0.540 | 1.412 | 3.018 | 3.003 |
| | STDEV | 0.038 | 0.143 | 0.139 | 0.149 |
| 1mM | | 0.567 | 1.251 | 2.617 | 2.820 |
| | | 0.485 | 1.566 | 2.680 | 3.002 |
| | | 0.543 | 1.393 | 2.701 | 3.000 |
| | | 0.565 | 1.325 | 2.700 | 3.034 |
| | Average | 0.540 | 1.384 | 2.675 | 2.964 |
| | STDEV | 0.038 | 0.135 | 0.040 | 0.097 |
| 2mM | | 0.567 | 1.109 | 1.942 | 1.846 |
| | | 0.485 | 1.280 | 2.073 | 2.564 |
| | | 0.543 | 1.211 | 2.205 | 2.398 |
| | | 0.565 | 1.376 | 2.239 | 2.129 |
| | Average | 0.540 | 1.244 | 2.115 | 2.234 |
| | STDEV | 0.038 | 0.113 | 0.136 | 0.315 |
| 3mM | | 0.567 | 0.819 | 1.374 | 1.242 |
| | | 0.485 | 1.066 | 1.172 | 1.366 |
| | | 0.543 | 1.108 | 1.606 | 1.172 |
| | | 0.565 | 1.154 | 1.371 | 0.994 |
| | Average | 0.540 | 1.037 | 1.381 | 1.194 |
| | STDEV | 0.038 | 0.150 | 0.177 | 0.155 |
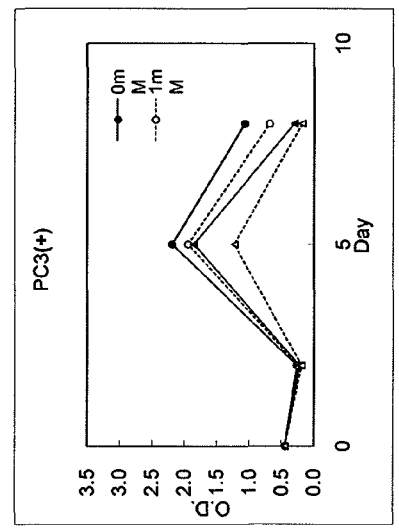

ACTIVATED FOAM

This application is a Divisional of U.S. application Ser. No. 10/582,801, filed Jul. 11, 2006 now abandoned, which is the National Stage of International Application No. PCT/JP2005/008906, filed May 16, 2005.

TECHNICAL FIELD

The present invention relates to an activated foam made of natural or synthetic rubber or synthetic resin, and to an activated foam capable of facilitating blood circulation and promoting the improvement of physical condition and the cure of diseases such as cancer.

BACKGROUND ART

Prostate cancer is a typical male cancer occurring at old age, and has increased also in Japan due to the aging of the population and the westernization of life style. In addition, an upward trend thereof has been confirmed because of an advanced blood test using tumor markers (prostate specific antigen: PSA) and a more generalized medical examination. When the age-adjusted incidence rate (per 100,000 people) of prostate cancer in Japan is looked at, it is only 3.5 for 1956, but 8.5 for 1990, and is statistically estimated to reach 20.3 in 2015.

In North America, the incidence rate of prostate cancer is strikingly high, and is 92.4 for 1990, and third-generation Japanese in the United States have an incidence rate of prostate cancer close to that of Caucasians in North America. It is not too much to say, also from this fact, that the westernization of life style including a meal with excessive fat is linked with the increase in prostate cancer in Japan. Thus, it is predicted that the prostate cancer of 80,000 to 100,000 people will be amenable to treatment in 2015.

Statistics by NCI (National Cancer Institute) in 1998 to 2002 show that the age-adjusted incidence rate (per 100,000 people) of cancers for all sites was 469.7 in the United States. Among these cancers, prostate cancer has the rate of 76.0, holding the first rank, followed by breast cancer (73.3), pulmonary or bronchial cancer (61.0), large bowel cancer (38.3), and lymphoma (21.8) which hold the 5th rank or above. Prostate cancer is characterized in that androgen induces the growth thereof while removal of androgen suppresses the growth. Therefore, in order to suppress the growth of prostate cancer, the removal of the testes through surgery or the application of an anti-androgen therapy in which the function of the testis is inhibited by a pharmaceutical agent is often carried out. However, the anti-androgen therapy will result in the recurrence of prostate cancer at some future time although it can suppress the clinical progress thereof over a certain period of time (typically, 1 to 3 years). The hormone therapy results in a ten-year survival rate of 10% or less when metastasis is present in a distant organ (often in the bone).

For localized prostate cancer, radical total prostatectomy (including the removal of the regional lymph node in the pelvis) literally provides a radical therapy. In addition to surgical therapy, there are a wide choice of options from hormone therapy to radiation therapy including heavy particle irradiation and direct implantation of an acicular radioactive material in the prostate and to chemotherapy using anti-cancer agents, depending on the degrees of malignancy and progress of prostate cancer and the presence of the metastasis thereof.

DISCLOSURE OF THE INVENTION

Problems to be Solved by the Invention

However, any of the therapies has complications and adverse effects while it has not a few cases in which the recurrence thereof cannot be avoided. Thus, there is need for the development of an effective therapy free of adverse effect. In addition, there is an ultimate need for a preventive remedy for prostate cancer; it has been recently reported in the United States that the take of vitamin E was effective in inhibiting the incidence of prostate cancer in large-scale clinical trials. In actual fact, the histological examination of the prostate in autopsy cases who died from other causes often leads to the discovery of prostate cancer, which is called latent cancer. Latent cancer has a high incidence, and is found in about 30 percent of the age group of 50 upward although it is different between reports when cancers histologically showing an invasion are included. The age group of 80 upward is noted to have prostate cancer in about 60 to 70 percent thereof. There is an urgent need for the development of a method of prevention so that the latent cancer does not become clinical cancer.

In view of the above-described problems, an object of the present invention is to provide an activated foam having no adverse effect and capable of facilitating blood circulation and promoting the improvement of physical condition and the cure of diseases such as cancer.

Means for Solution of the Problems

As a result of earnest studies for solving the above-described problems, the present invention is accomplished. Specifically, the invention relates to an activated foam made of natural or synthetic rubber or synthetic resin, characterized in that the foam contains a zirconium compound and/or a germanium compound, and has a closed-cell structure, wherein the foam is used so as to directly or indirectly contact with a human body when a pharmaceutical agent is administered.

The activated foam of the invention is used by the direct or indirect contact thereof with a human body, which is more effective when further producing friction between the foam and the body. The activated foam can facilitate blood circulation and promote the improvement of physical condition and the cure of diseases, but a mechanism therefore has not been elucidated.

The zirconium compound and the germanium compound collect infrared rays e.g. from the sun into the activated foam. Then, the infrared rays impinge on the walls of many cells inside the activated foam for repeating diffuse reflection and aggregation, and there are thereby radiated, toward the outside of the activated foam, infrared rays having wavelengths of 4 to 25 microns which exert a favorable influence on a human body. It is speculated that these infrared rays resonate with the wavelengths of a human body to activate a water molecule and protein molecules in the body to enhance, through the excitometabolic effect, natural healing power originally possessed by humans. Thus, it is thought that the cure of diseases such as cancer, hypertension, diabetes, heart disease, stiffness in the shoulder, low back pain, and allergic disease, and the improvement of physical condition, e.g. prevention from getting older or hair restoration are facilitated. In addition, the activated foam can be repeatedly used.

The activated foam of the invention may be used, in administering a pharmaceutical agent, by directly or indirectly contacting it with a human body to increase the effect of the pharmaceutical agent. In addition, even a pharmaceutical agent which would exert an adverse effect in a large dose, if it is combined with an ordinal use of the activated foam, may reduce the adverse effect because its dosage can be decreased.

Non-limiting examples of the pharmaceutical agent include an injection agent, a skin agent for external use, a mucocutaneous agent, a nasal agent, and an oral agent. More specific examples thereof include, but not limited to, an anticancer agent and an antibiotic. The pharmaceutical agent is preferably a human-derived substance. The term "human-derived" substance refers to a substance which a human originally has in the body. In this respect, the human-derived substance may be extracted from a human body or artificially synthesized.

Among human-derived substances, a substance having the least possible adverse effect is preferably used because it has no adverse effect when used at a normal dose. Examples thereof include sodium butyrate (hereinafter referred to as SB) and sodium butyric butyrate ester which are present in the human intestine. These substances are inhibitors of histone deacetylase (HDACI or HDi for short; hereinafter abbreviated as HDACI) deactivating chromatin, and activate chromatin to express a cancer suppressor gene to serve to arrest the cell cycle (division cycle; the life cycle of a cell from the completion of cell division to the next cell division) of a cancer cell, that is, act as anti-tumor agents. SB and a butyrate ester derivative which have been synthesized are also useful if they are less toxic. Combination of the take of any of these substances and the use of the activated foam can suppress the function of an oncogene and increase the cancer-suppressing effect thereof.

In addition, the human-derived substances may be various nuclear transcription factors (DNA activator and suppressor) and a chromatin-remodeling substance which act cooperatively together with HDACI. That is, they may be any substance acting on the promoter region of the DNA of the cancer suppressor gene so as to activate the suppressor gene. These substances may be also combined with the activated foam to suppress the function of the oncogene to increase the cancer-suppressing effects thereof.

Cells contained inside the foam are preferably formed at a density of 20 to 30 cells/mm$^2$. Many closed cells may be thus contained at high density to generate infrared rays exerting a favorable influence on a human body.

The form of the activated foam may be a small, portable and handy triangle, bedclothing-like form such as a mat to lay on or a mat to cover, or as a portion or the whole e.g. of a suit, but is not limited thereto if the form makes it possible for the foam to directly or indirectly contact with a human body. If it is desired to give such effects as for curing diseases, concentrated locally on a portion of a human body, the activated foam could be formed into a sheet shape having a thickness of about 8 mm to 5 cm. When it is used as a clothing material, forming the foam into a sheet shape having a thickness of about 0.3 to 5 mm facilitates the making thereof into clothing.

The rubber component may be natural rubber or synthetic rubber. Non-limiting examples of the synthetic rubber include rubbery polymers such as chloroprene rubber (CR), styrene-butadiene rubber (SBR), acrylonitrile-butadiene rubber (NBR), acrylonitrile rubber (NRP), butadiene rubber (BR), and isoprene rubber (IR), or a mixture of plural kinds thereof.

Non-limiting examples of the synthetic resin component include vinyl chloride resin (PVC), polypropylene (PP), and polyethylene (PE).

A foaming agent may use a well-known foaming agent, but is preferably Celogen OTI (from Uniroyal, U.S.A.) or Unicell (from Dongjin, South Korea).

The activated foam may contain both or either of the zirconium compound and the germanium compound. For cancer treatment, both of the zirconium compound and the germanium compound are preferably contained because the effect of facilitating the cure of cancer is enhanced.

The zirconium compound preferably uses a zirconium complex compound. Examples of the zirconium complex compound include a complex of zirconium and fluorine or the like; specific examples thereof include, but not limited to, potassium hexafluorozirconate ($K_2ZrF_6$) and potassium octafluorozirconate ($K_2ZrF_8$). The content of the zirconium compound is preferably 10 to 80 parts by weight, based on 100 parts by weight of rubber component. A content thereof lower than the lower limit results in poor effect, and a content thereof higher than the upper limit is undesirable from the economic standpoint because no significant difference in effect is produced.

The germanium compound preferably uses a germanium mineral or a germanium complex compound. Non-limiting examples of the germanium mineral include argyrodite ($Ag_8GeS_9$) and renierite (($Cu, Zn)_{11}Fe_4(Ge, As)_2S_{16}$). Non-limiting examples of the germanium complex compound include a complex of germanium and dicarboxylic acid or amine. The content of the germanium compound is preferably 5 to 10 parts by weight, based on 100 parts by weight of rubber component. A content thereof lower than the lower limit results in poor effect, and a content thereof higher than the upper limit is undesirable from the economic standpoint because no significant difference in effect is produced.

In addition to the above-described components, the activated foam preferably contains carbon. The containing of carbon increases the strength of the activated foam, and enables more infrared rays e.g. from the sun to be collected. Non-limiting examples of the carbon include carbon black which may be used in granular form.

Advantages of the Invention

According to the invention, in administering a pharmaceutical agent, the activated foam may be used by directly or indirectly contacting it with a human body to increase the effect of the pharmaceutical agent. In addition, even a pharmaceutical agent which would exert an adverse effect in a large dose, if combined with the activated foam, may reduce the adverse effect because its dosage can be decreased.

BRIEF DESCRIPTION OF THE DRAWINGS

FIG. 8 is a pair of tables with graphs showing changes with time in the number of live cells of Du145 (human prostate cancer cell); (+) shows an experimental group using the activated foam of the invention, and (−) a control group;

FIG. 9 is a pair of tables with graphs showing changes with time in the number of live cells of LNCap (human prostate cancer cell); (+) shows an experimental group using the activated foam of the invention, and (−) a control group; and FIG. 10 is a pair of tables with graphs showing changes with time in the number of live cells of PC3 (human prostate cancer cell); (+) shows an experimental group using the activated foam of the invention, and (−) a control group.

DESCRIPTION OF SYMBOLS

1 Foamed sheet
2 Cover sheet

BEST MODE FOR CARRYING OUT THE INVENTION

Figure 1:
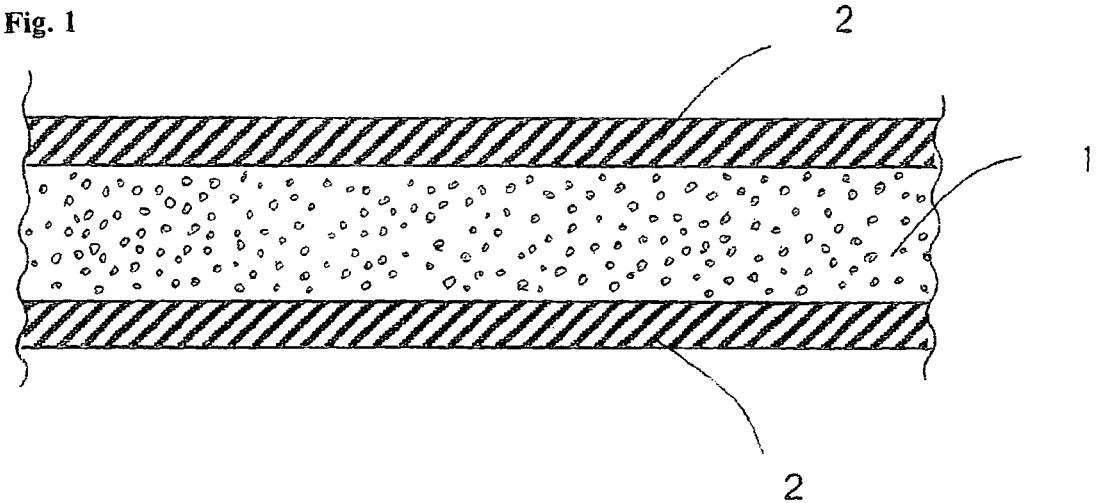
FIG. 1 is a longitudinal sectional view of an activated foam of an embodiment of the present invention.
Figure 2:
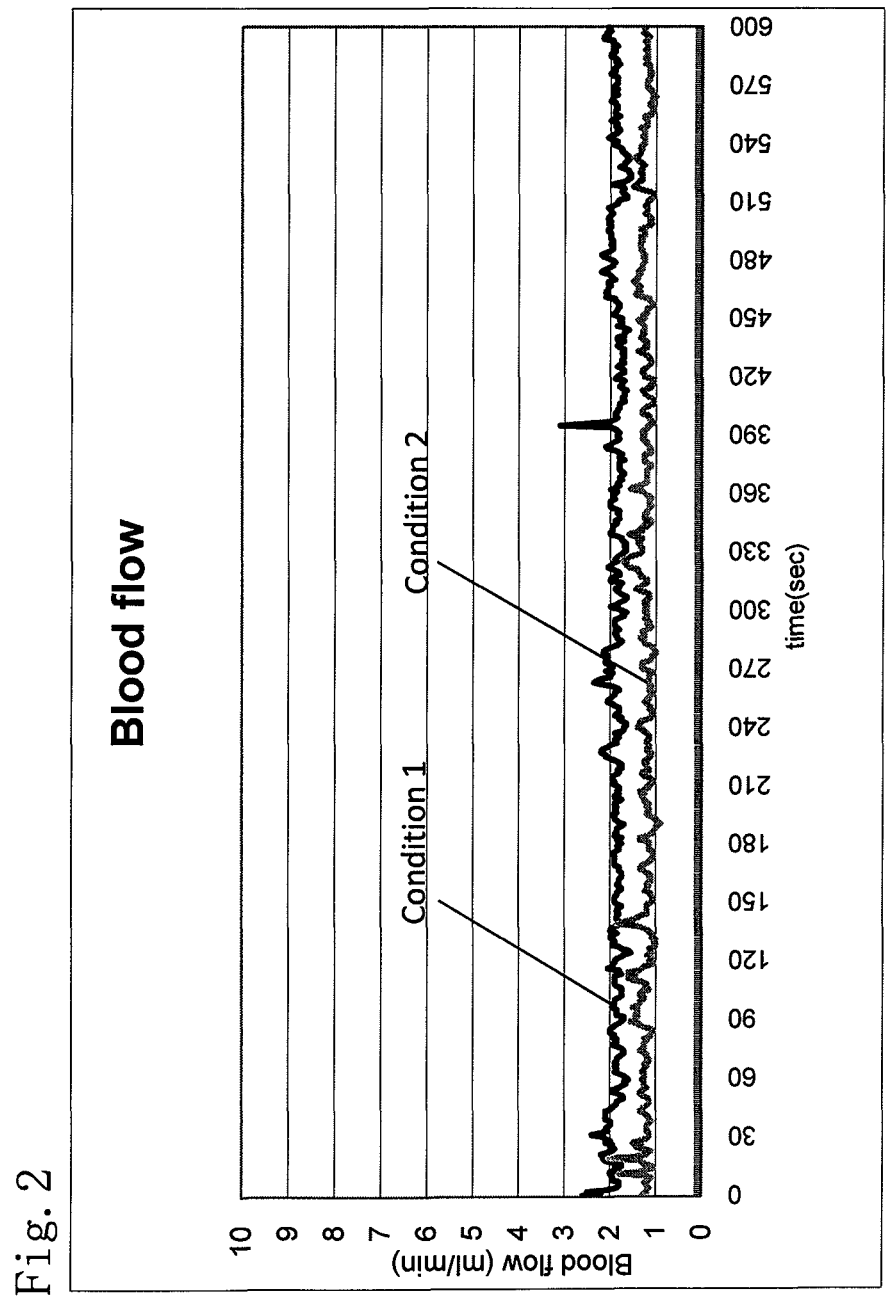
FIG. 2 is a graph showing a change in blood flow (ml/min/100 g)
Figure 3:
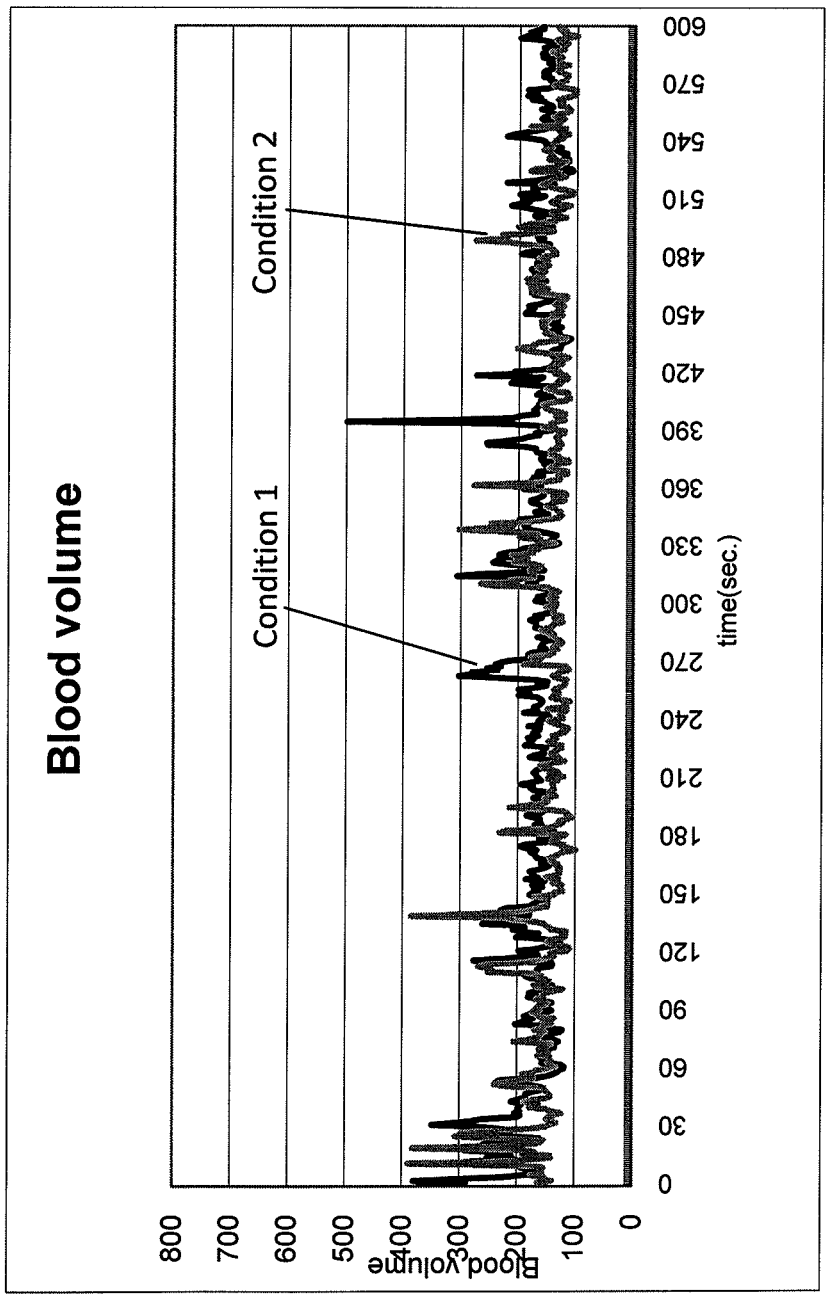
FIG. 3 is a graph showing a change in blood volume.
Figure 4:
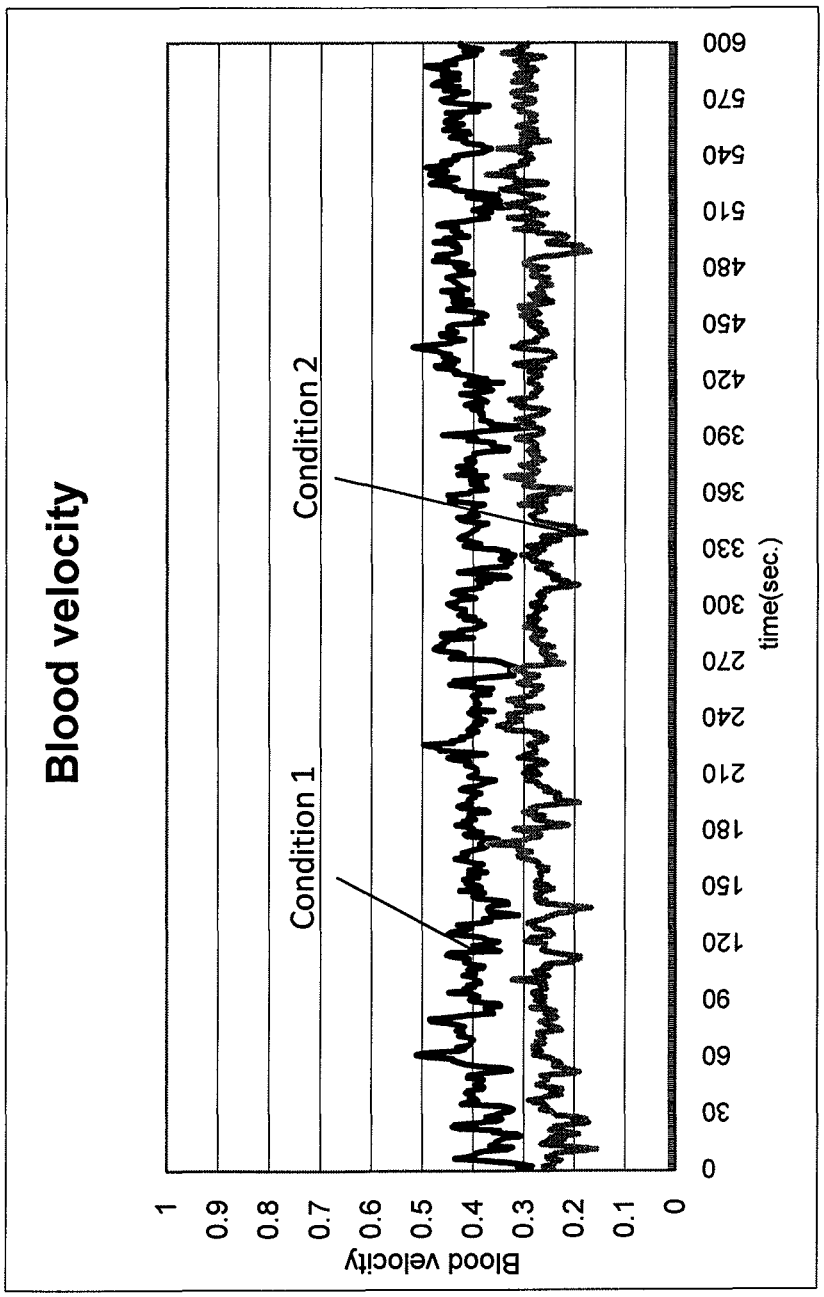
FIG. 4 is a graph showing a change in blood velocity.
Figure 5:
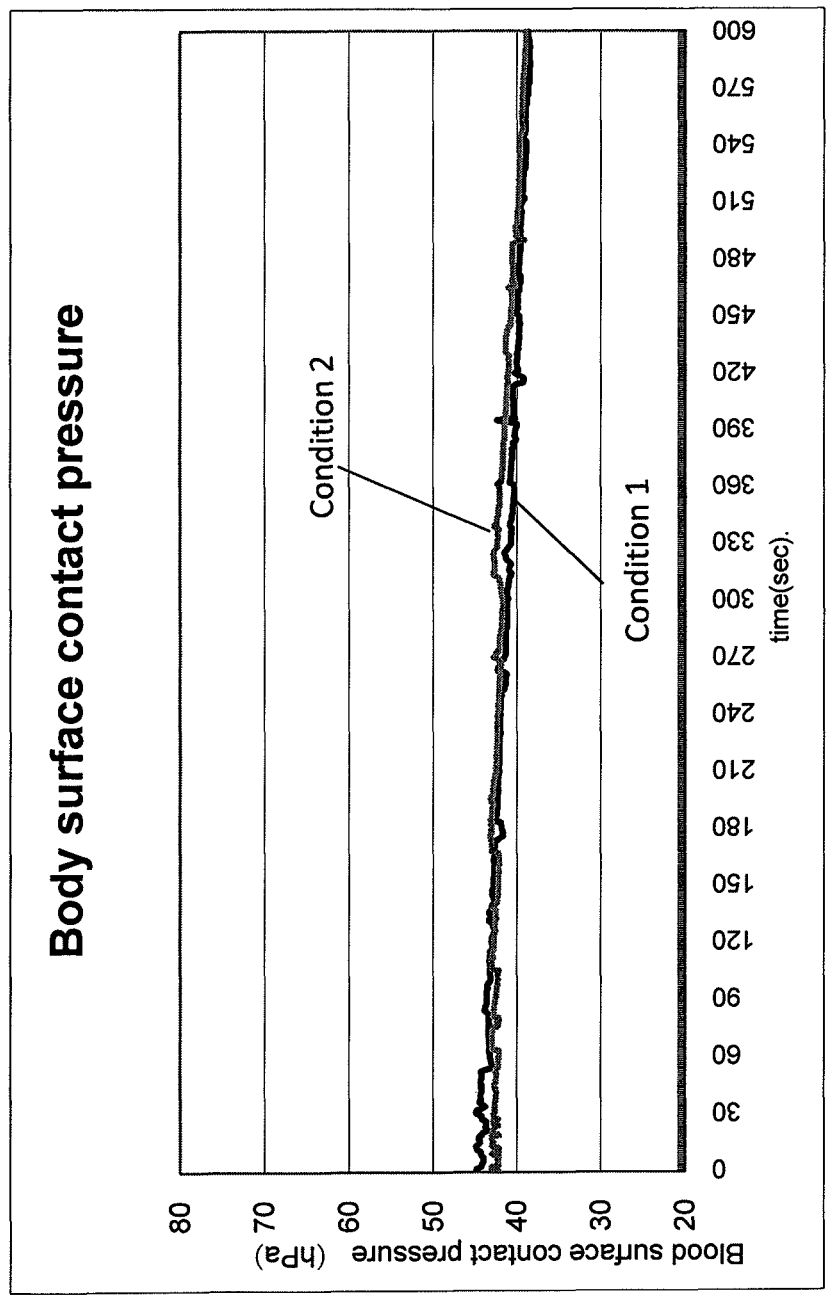
FIG. 5 is a graph showing a change in body surface contact pressure (hPa)

Embodiments of the invention will be described below based on the drawings. FIG. 1 is a longitudinal sectional view of an activated foam of an embodiment of the present invention. As shown in FIG. 1, the activated foam of an embodiment of the present invention is a laminate consisting of rubber cover sheet 2 laminated on both sides of rubber foamed sheet 1. Although the embodiment takes the form of cover sheet 2 laminated on both sides of rubber sheet 1, there may be taken the form of cover sheet 2 laminated on either side of rubber sheet 1 or the form of only foamed sheet 1 without laminating cover sheet 2.

Foamed sheet 1 is a foam which mainly comprises rubber or synthetic resin, contains a zirconium compound and/or a germanium compound and carbon, and has a closed-cell structure. The closed cell is formed by foaming with a foaming agent. The cross-section of foamed sheet 1 has a large number of fine cells formed. The thickness of foamed sheet 1 is set to about 1 cm, but not intended to be limited thereto.

Cover sheets 2 are fixed by adhesion to both sides of foamed sheet 1, but the fixation may be carried out by another method in so far as they can be laminated on foamed sheet 1. In addition, the material of cover sheet 2 is a rubber sheet mainly comprising chloroprene rubber (CR), which contains no cell, but may take a form containing cells. Further, the material of cover sheet 2 is not limited to chloroprene rubber and may be another synthetic rubber, natural rubber, or a synthetic resin such as chlorosulfonated polyethylene.

EXAMPLE

Specific aspects of the invention will be described below in detail, based on Example. However, this invention is not intended to be limited to Example below, and it is believed obvious that various modifications and variations may be made in Example as fall within the scope of the invention.

Foamed sheet 1 is first prepared. Rubber or synthetic resin is used as a base, and compounding is carried out according to the formulation in Table 1, followed by kneading with a roll. In this respect, a method for mixing materials is not particularly restricted, and may use a conventional mixing method as employed for a rubber or synthetic resin compound. The resultant kneaded matter is then formed into sheet form using an extruder. This sheet is vulcanized and expanded using a heated air (vulcanizing process). The vulcanizing process is carried out in primary and secondary two stages. The two-stage vulcanization leads to uniform formation of cells throughout the foamed sheet. The above process results in the production of foamed sheet 1.

Cover sheet 2 is then sticked on both sides of foamed sheet 1 using a rubber- or synthetic resin-based adhesive. Subsequently, a high voltage is applied to the side providing the front thereof. The voltage application is carried out under the conditions of a current of 10,000 to 800,000 amperes, a voltage of 200 to 3,300 V, and a duration of 0.1 to 0.3 second. In this respect, a higher current is more preferable. The activated foam generates electromagnetic waves such as infrared rays. It is believed that the high voltage is applied to one side of the activated foam to direct the electromagnetic wave so as to show directivity toward the surface side to which the voltage has been applied, although the mechanism has not been elucidated. Accordingly, contact of the surface with a human body enables electromagnetic waves to be irradiated in a concentrated manner on the contact area thereby enhancing the effect of curing disease or the like. The above process allows the activated foam to be completed.

TABLE 1

|  | Example 1 | Example 2 | Example 3 | Example 4 | Example 5 | Example 6 |
|---|---|---|---|---|---|---|
| Natural rubber | 100 |  |  |  |  |  |
| Chloroprene rubber |  | 100 |  |  | 100 |  |
| Chlorosulfonated polyethylene |  |  | 100 |  |  |  |
| PVC (vinyl chloride resin) |  |  |  | 100 |  |  |
| NRP (acrylonitrile rubber) |  |  |  |  |  | 100 |
| Liquid nitrile rubber |  |  |  |  |  | 6 |
| Zirconium complex compound | 10 | 20 | 7 | 80 |  | 30 |
| Zircon |  | 2 | 20 |  | 30 |  |
| Germanium complex compound |  | 10 | 10 |  |  |  |
| Stabilizer |  |  |  | 3 |  |  |
| Zinc oxide | 5 | 5 | 5 |  | 5 | 5 |
| Magnesium oxide | 3 | 3 | 3 |  | 3 |  |
| Celogen OTI | 10 | 10 | 10 | 10 | 10 |  |
| Stearic acid |  |  |  |  |  | 3 |
| DOP (plasticizer) |  |  |  | 25 |  | 30 |
| Carbon black | 25 | 20 | 20 |  | 20 |  |
| Process oil | 30 | 30 | 5 |  | 30 |  |
| Sulfur | 3 |  |  |  |  | 3 |
| Vulcanization accelerator DM | 2 |  |  |  |  | 3 |
| Silicon oxide | 12 |  |  | 12 |  | 20 |
| Vulcanizing condition |  |  |  |  |  |  |
| Primary | 130° C. × 10 min | 132° C. × 19 min | 120° C. × 8 min | 160° C. × 5 min | 100° C. × 10 min | 130° C. × 10 min |
| Secondary | 160° C. × 10 min | 160° C. × 10 min | 150° C. × 8 min | 100° C. × 5 min | 160° C. × 10 min | 160° C. × 10 min |
| Apparent specific gravity | 0.16 | 0.21 | 0.35 | 0.24 | 0.22 | 0.2 |
| Hardness | 7 | 8 | 10 | 10 | 9 | 9 |

(Unit: parts by weight)

In Example above, Celogen OTI is p,p'-oxybis(benzenesulfonyl)hydrazine (from Uniroyal, U.S.) which is a foaming agent. "Zircon" typically means zircon present in the form of silicate ($ZrSiO_4$). "Vulcanization accelerator DM" refers to dibenzothiazole disulfite. The hardness was determined using a rubber hardness tester (type C).

<Test 1>

The activated foam was then used to perform a test for determining effects thereof on body surface contact pressure and blood flow in a human. A method for measuring body surface contact pressure and blood flow will first be described.

[Test Subject]

One female aged in her fifties was used as a subject.

[Test Method]

The test was carried out using an instrument for measuring blood flow and body surface contact pressure (AMI3037-2, from AMI Technology). A body surface contact pressure/blood flow sensor was attached to the upper part of the thigh for measurement in the environment of a room temperature of 23° C. and a humidity of 55% RH under the following two conditions. In condition 1, the activated foam was spread on a chair, on which the subject then sat in resting state for 30 minutes, followed by measuring blood flow, blood volume, blood velocity, and body surface contact pressure for 10 minutes. In condition 2, the subject sat, for control, on a chair on which the activated foam was not spread for 30 minute, followed by measuring blood flow and the like for 10 minutes. The results are shown in Table 2 and FIGS. 2 to 5. Table 2 shows the mean values of measurements of blood flow and the like for 10 minutes. FIGS. 2 to 5 show changes with time in blood flow and the like for 10 minutes. In this respect, "blood flow" refers to blood flow per 100 g of human body tissue per minute, and is determined from the amount of light reflected by red blood cells in capillary vessels. "Blood volume" refers to blood volume per cross-sectional area of 100 g of human body tissue, and the product of the blood volume and the blood velocity becomes nearly equal to the blood flow.

[Test Results]

TABLE 2

|  | Blood flow (ml/min. 100 g) | Blood volume | Blood velocity | Body surface contact pressure (hPa) |
|---|---|---|---|---|
| Condition 1 | 1.882 | 172.12 | 0.406 | 40.47 |
| Condition 2 | 1.232 | 150.53 | 0.272 | 42.74 |

As shown in Table 2 and FIGS. 2 to 5 above, the use of the activated foam improves blood circulation and reduces body surface contact pressure.

<Test 2>

[Test Subjects]

Cultures of human-derived prostate cancer cell lines Du145, PC3, and LNCap were used. LNCap is a hormone-dependent prostate cancer cell, and Du145 and PC3 are hormone-independent prostate cancer cells.

[Test Method]

On culture plates 10 cm in diameter in each of which 15 ml of medium was placed were spread $10^5$ cells/plate each of prostate cancer cells (Du145, LNCap, and PC3) to culture under conditions of 37° C. and 5% $CO_2$ for 7 to 10 days (preparatory period), followed by starting the test. In this respect, one kind of prostate cancer cell should be spread on one culture plate. In addition, the activated foam is not used during the preparatory period.

After starting the test, culture was carried out, in an experimental group, in a state holding each culture plate from the upper and lower sides thereof using the activated foams. In a control group, the culture was performed in a state free of the activated foam. The culture medium was exchanged every 3 days on average, and each kind of cell was subcultured on a new plate before the cells became confluent. A subculture date was different between the above kinds of cells, but the same between the control and experimental groups of each thereof.

A day immediately before the start of test was set to day 0, and cells were collected at the 1st, 2nd, and 3rd week after the start of test. Cells at the 3rd week of culture were fixed and then electron-microscopically observed (a).

In addition, mRNA (messenger ribonucleic acid) was extracted from the cells at the 3rd week of culture. The extracted mRNA was hybridized to a human 1.2K cDNA microarray (Clontech), followed by analyzing the results using GeneSpider (gene-finding software: Silicon Genetics, Redwood, Calif., U.S.A.). The expression of a gene responsible for apoptosis was determined using ANOVA cluster analysis (b).

[Test Results]

It was noted in the experimental group that the proliferation of each kind of prostate cancer cell had the following characteristics.

Figure 6:
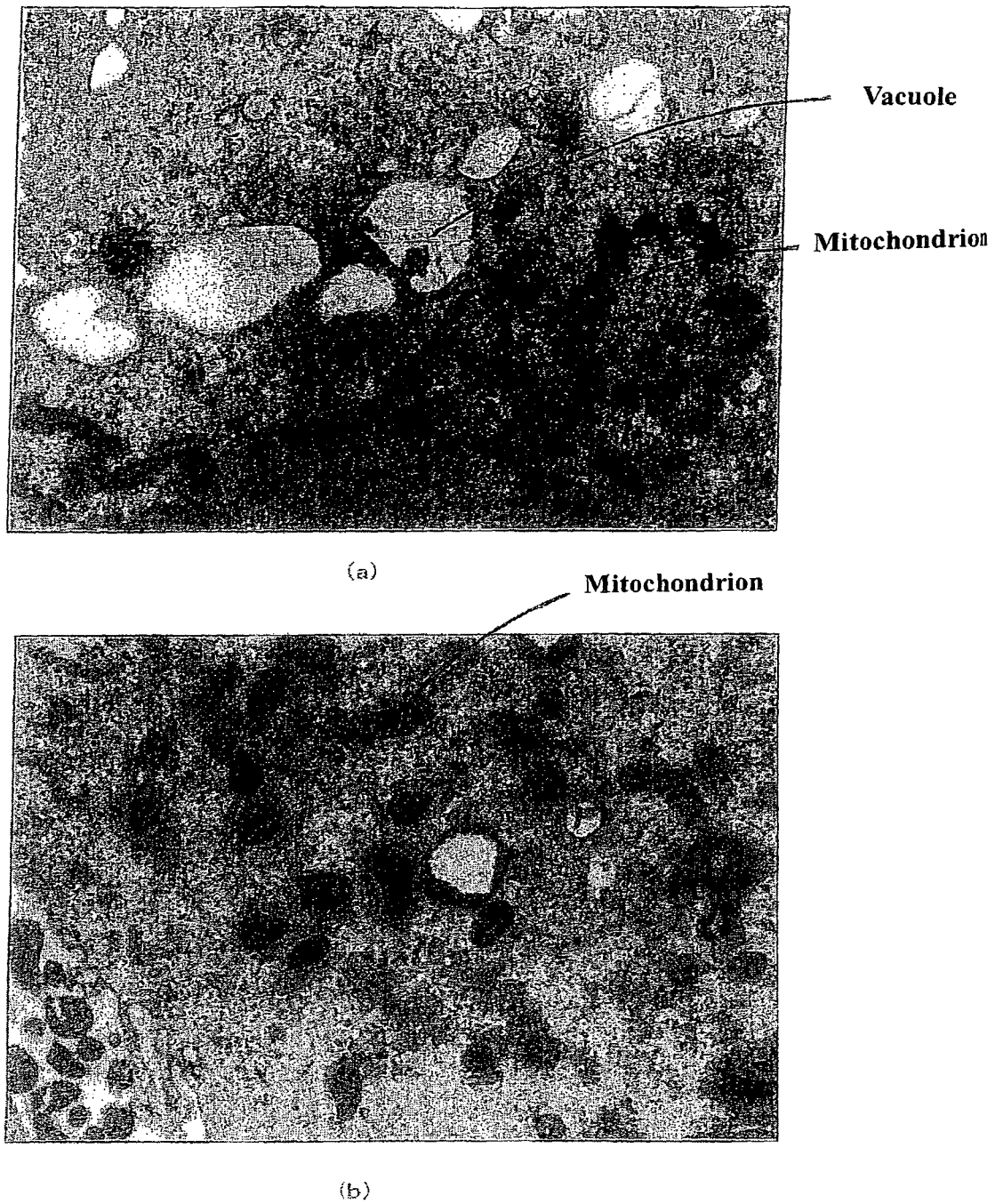
FIG. 6 is a pair of electron micrographs of cells; (a) experimental group, (b) control group.

(a) A morphological difference was observed between electron-microscopic appearances at the 3rd week in the experimental and control groups. Specifically, each cancer cell having contacted the activated foam for 3 weeks had more cytoplasmic vacuoles, less visible internal structures of mitochondria, and a less clear nuclear membrane (FIG. 6(a)) relative to that of the control group (FIG. 6(b)). Thus, it is shown that apoptosis occurs in the cells in which the activated foam has been used.

The term "apoptosis" refers to genetically programmed cell death, i.e., the suicide of a cell. A cancer cell means a cell which continues proliferation because the apoptosis system is out of order.

Figure 7:
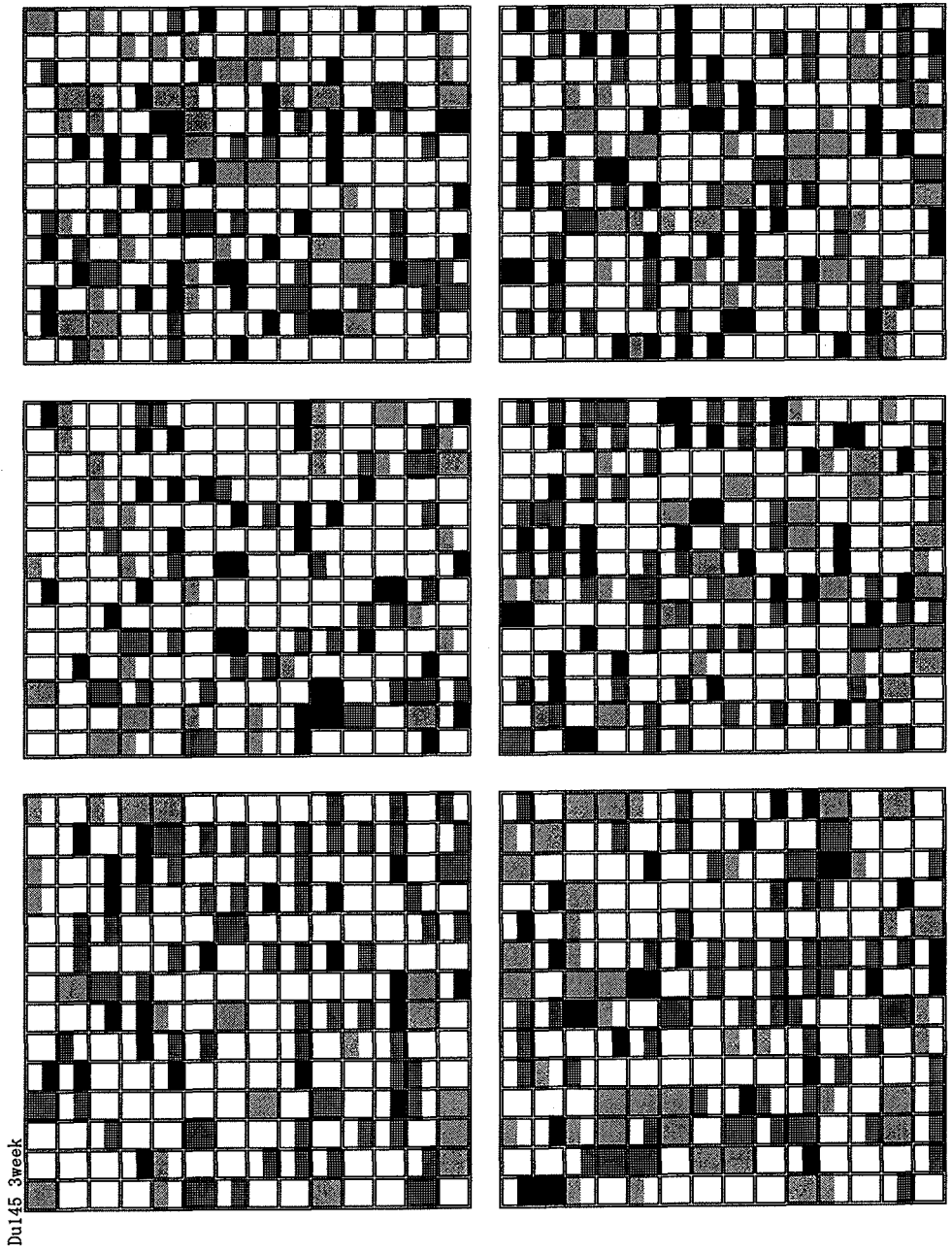
FIG. 7 is a result of cDNA microarray analysis in live cells of Du145 (human prostate cancer cell)

(b) The results with DU145 are shown in FIG. 7, as a representative example for the results of cDNA microarray at the 3rd week. Black color indicates enhanced mRNA expression relative to that of the control group, i.e., the activation of a gene; lattice pattern indicates lowered mRNA expression relative to that of the control group, i.e., the reduced function of a gene; and gray color indicates unaltered mRNA expression relative to that of the control group.

For Du145, the experimental group showed up-regulation in FasL (2.3 fold), Fas (1.4 fold), TRADD (1.4 fold), CASP1, 4, and 10 (1.7, 1.2, and 1.7 fold), and DFF40 (1.7 fold) compared to the control group. For PC3, the experimental group showed up-regulation in CD40 (1.4 fold) and TNF (1.4 fold) compared to the control group. For LNCap, the experimental group showed up-regulation in Fas (1.6 fold), CASP8 (1.6 fold), and CASP3 (1.3 fold) compared to the control group. In this respect, FasL, Fas, TRADD, CASP1, 4, and 10, DFF40, CD40, and TNF form a gene group which starts up the apoptosis circuit. These results show that apoptosis is facilitated in the experimental group using the activated foam compared to that in the control group.

[Discussion]

The following can be said from the above-described test results. The activated foam starts up the apoptosis circuit and facilitates the effect of weakening the function of cancer cells.

<Test 3>

The activated foam and SB as HDACI were used against human prostate cancer cells to carry out a cancer cell proliferation suppressing test. This test can be used to specifically reveal a revolutionary method for treating or preventing prostate cancer and to suggest that it may be, in principle, effective against any cancer. HDACI will now be described in detail. Acetylation of lysine in histone by HAT (histone acetyl transferase) activates nuclear chromatin. The activation of the chromatin leads to the binding of a nuclear transcription factor, together with an activator, to a promoter region in DNA, resulting in the expression of a structural gene. In addition, HDAC (histone deacetylase) causes the deacetylation of lysine to again inactivate the chromatin.

HDACI typified by SB prevents the deacetylation by HDAC to eliminate the inactivation of the chromatin. Thus, HDACI activates a cancer suppressor gene and the like whose functions are weakened to act so as to suppress the proliferation of cancer cells.

[Test Subjects]

Cultures of human-derived prostate cancer cell lines Du145, PC3, and LNCap were used. LNCap is a hormone-dependent prostate cancer cell, and Du145 and PC3 are hormone-independent prostate cancer cells.

[Test Method]

Each kind of prostate cancer cell (Du145, LNCap, or PC3) was cultured at a concentration of $10^3$ cells/100 μl in a 96-well microplate. In an experimental group, 6 μl of 0, 1, 2, or 3 mM SB was added to the plate, and the plate was held from the upper and lower sides thereof using the activated foams. The SB-containing culture medium was exchanged every two days. In a control group, the culture was carried out without using the activated foam while 6 μl of 0, 1, 2, or 3 mM SB was added. The 0 mM SB consisted of the same amount (6 μl) of PBS (phosphate buffered saline). The above-described test was performed in quadruplicate for each concentration.

At the 2nd, 5th, and 8th day of culture, live cells were determined at an optical density (O.D.) of 450 nm using Cell Proliferation Kit II (XTT: from Roche, Manheim, Germany) (in which the value (650) of a blank was subtracted).

Cell Proliferation Kit II (XTT) uses the property that XTT is a substrate for dehydrogenase and reduced into formazan by the dehydrogenase to determine a formazan dye generated by an XTT standard mixture and a mitochondrial dehydrogenase activity for quantifying the survival rate of cells. Thus, the amount of formazan corresponds to the number of live cells.

[Test Results]

The activated foam significantly suppressed the proliferation of each kind of human prostate cancer cell irrespective of the presence of the hormone dependency thereof in the presence of even a low concentration (1 mM) of SB compared to that in the presence of a high concentration (3 mM) of SB without the activated foam (FIGS. 8 to 10). That is, the activated foam acted in association with SB to distinctly suppress the proliferation of human prostate cancer cells.

[Discussion]

The following can be said from the above-described test results. As shown in FIGS. 8 to 10, the activated foam can be used simultaneously with HDACI to facilitate the suppressive effect of HDACI against proliferation of human prostate cancer cells. In principle, this method is thought to be an effective therapy against any cancer. In addition, SB is a substance which is present in the intestine in a human body and induces no allergic reaction. Thus, the 1 mM concentration thereof demonstrated to be effective in the present test has extremely low toxicity against a living body and is free of adverse effects such as allergy.

In addition, surplus HDAC cooperates with chromatin remodeling factor and the like to methylate cytosine and suppress the proliferation of cancer cells.

INDUSTRIAL APPLICABILITY

The activated foam of the invention may be used, in administering a pharmaceutical agent by directly or indirectly contacting it with a human body to increase the effect of the pharmaceutical agent. In addition, even a pharmaceutical agent which would exert an adverse effect in a large dose, if combined with the activated foam, may reduce the adverse effect because its dosage can be decreased.

The invention claimed is:

1. A method of increasing an effect of an anti-cancer pharmaceutical agent in a patient, comprising:
    contacting the patient with a material consisting of an activated foam having cells with a closed-cell structure made of a natural or synthetic rubber or a synthetic resin, and a zirconium compound and/or a germanium compound; and
    optionally, a cover sheet laminated on at least a side of the activated foam;
    wherein the patient is simultaneously administered the anti-cancer pharmaceutical agent, the anti-cancer pharmaceutical agent is sodium butyrate or butyrate ester, and
    the material is at room temperature when contacted with the patient.

2. A method of increasing an effect of an anti-cancer pharmaceutical agent in a patient, comprising:
    contacting the patient with an activated foam comprising cells with a closed-cell structure made of a natural or synthetic rubber or a synthetic resin, and a zirconium compound and/or a germanium compound, and carbon;
    wherein the patient is simultaneously administered the anti-cancer pharmaceutical agent, the anti-cancer pharmaceutical agent is sodium butyrate or butyrate ester, and
    the activated foam is at room temperature when contacted with the patient.

3. The method according to claim 1, wherein said cells with a closed-cell structure are formed at a density of 20 to 30 cells/mm$^2$.

4. The method according to claim 2, wherein said cells with a closed-cell structure are formed at a density of 20 to 30 cells/mm$^2$.

5. A method of increasing an effect of an anti-cancer pharmaceutical agent in a patient, comprising:
    contacting the patient with an activated foam comprising a natural or synthetic rubber or a synthetic resin, a germanium compound and, optionally, a zirconium compound,
    wherein the patient is simultaneously administered the anti-cancer pharmaceutical agent, the anti-cancer pharmaceutical agent is sodium butyrate or butyrate ester, and
    the activated foam is at room temperature when contacted with the patient.

6. The method according to claim 5, wherein said cells with a closed-cell structure are formed at a density of 20 to 30 cells/mm$^2$.

* * * * *